United States Patent [19]

Larsen et al.

[11] 4,277,177
[45] Jul. 7, 1981

[54] APPARATUS TO MEASURE SELECT PROPERTIES OF A MOVING SHEET

[75] Inventors: Tor G. Larsen, Saratoga; John J. Howarth, Monte Sereno, both of Calif.

[73] Assignee: Measurex Corporation, Cupertino, Calif.

[21] Appl. No.: 100,416

[22] Filed: Dec. 5, 1979

[51] Int. Cl.³ .......................................... G01N 21/47
[52] U.S. Cl. .................................. 356/431; 250/571; 356/446; 356/243
[58] Field of Search .............. 356/421, 422, 429, 430, 356/431, 445, 446, 448, 243; 250/571, 572, 559, 562, 563

[56] References Cited

U.S. PATENT DOCUMENTS

| 1,978,589 | 10/1934 | McFarlane | 250/562 |
| 3,476,482 | 11/1969 | Howard | 356/446 |
| 3,793,524 | 2/1974 | Howarth | 356/429 |
| 3,890,049 | 6/1975 | Collins et al. | 356/429 |
| 4,029,420 | 6/1977 | Simms | 356/446 |
| 4,033,698 | 7/1977 | Demsky et al. | 356/446 |

Primary Examiner—R. A. Rosenberger

Attorney, Agent, or Firm—Ronald Yin; Hal J. Bohner

[57] ABSTRACT

An apparatus to measure select properties such as color, brightness or gloss, of a moving sheet, is insensitive to flutter in the sheet. The apparatus comprises a housing to one side of said sheet. A source is located in the housing; the source is capable of emitting a beam of electromagnetic radiation which is aligned to impinge the sheet. The radiation is selected such that it is capable of being absorbed and being reflected by the select properties of the sheet. A collector is also located in the housing; the collector is capable of receiving a portion of the beam reflected from the sheet. A detector capable of measuring the select properties of the sheet based upon the radiation received by the collector is also provided. The housing is held at a constant distance from the sheet by a stream of fluid from the housing directed to impinge the sheet in a direction substantially perpendicular to the sheet. A standardization member is to the other side of the sheet. The standardization member is also held at a constant distance from the sheet by a stream of fluid from the member directed to impinge the sheet along a direction substantially perpendicular to the sheet and in linear alignment with the stream of fluid from the housing.

6 Claims, 2 Drawing Figures

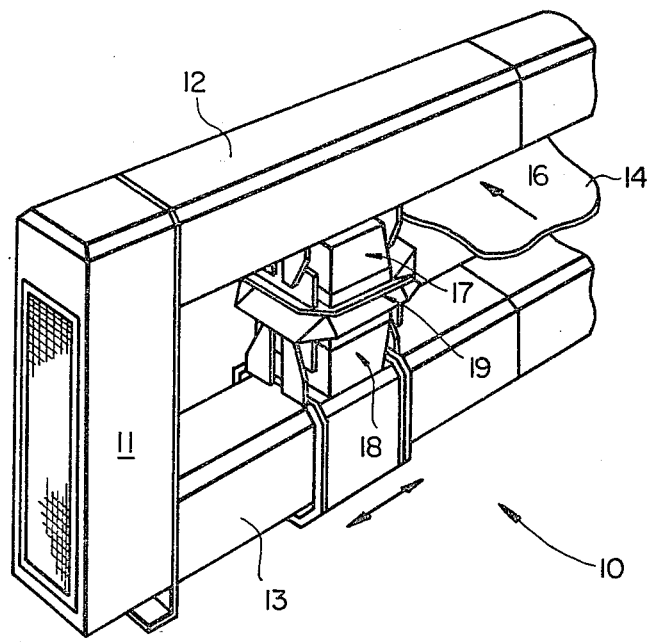
FIG_1
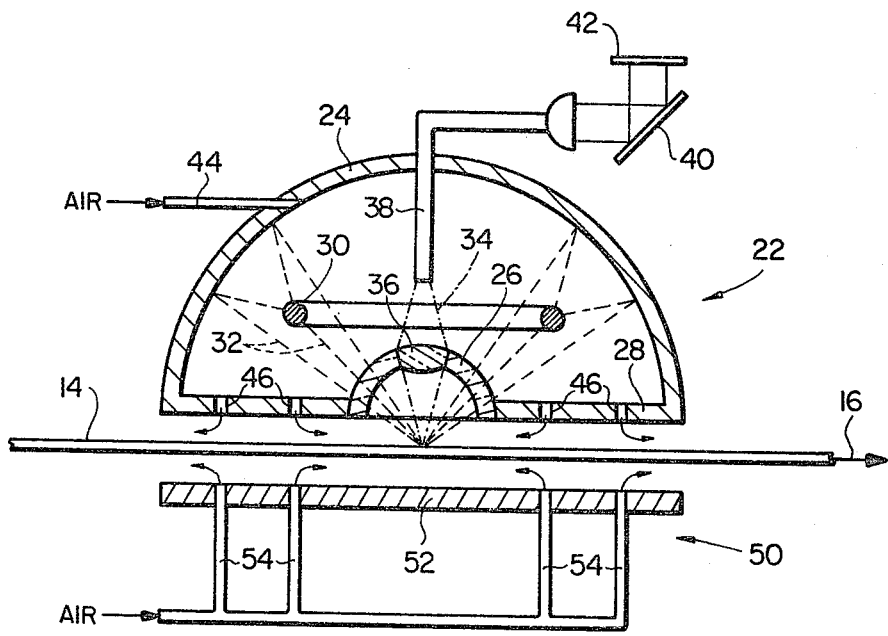
FIG_2

APPARATUS TO MEASURE SELECT PROPERTIES OF A MOVING SHEET

BACKGROUND OF THE INVENTION

The present invention is related to an apparatus for measuring select properties of a moving sheet. More specifically, the present invention is related to an apparatus capable of measuring select properties of a moving sheet with the apparatus insensitive to the flutter of the sheet.

Sensors to measure select properties, such as color, brightness, or gloss, of a moving sheet, are known. One such sensor to measure the color of a moving sheet is manufactured by the MacBeth Division of Kollmorgen Corporation. Typically, such a sensor does not scan, i.e., the sensor is not able to move across the width of the sheet as the sheet is being manufactured. Moreover, such a sensor cannot account for sheet flutter for accurate measurement. These constraints pose two problems: First, the sensor is unable to provide an accurate measurement across the width of the sheet; secondly, that the sensor cannot account for sheet flutter poses certain limitations in its application of use. Thus, the sensor of the prior art had limitations in its accuracy as well as in its applicability.

SUMMARY OF THE INVENTION

An apparatus to measure select properties of a moving sheet with the apparatus insensitive to the flutter of the sheet comprises a source to one side of the sheet. The source is capable of emitting a beam of electromagentic radiation which is aligned to impinge the sheet. The radiation is selected such that the beam is capable of being absorbed and being reflected by the select properties of the sheet. The apparatus is also provided with a detector capable of measuring the select properties of the sheet based upon the radiation received by the collector. First means are provided for holding the source and the collector at a constant distance from the sheet. A standardization member is located on the other side of the sheet. Second means are provided for holding the standardization member at a constant distance from the sheet.

BRIEF DESCRIPTION OF THE DRAWINGS

FIG. 1 is a partial perspective view of a portion of the apparatus for measuring the select properties of a moving sheet, incorporating the present invention, and FIG. 2 is a schematic representation partially in block diagram form and partially in cross-section of a portion of the apparatus of FIG. 1 and showing the apparatus of the present invention.

DETAILED DESCRIPTION OF THE INVENTION

As disclosed in the U.S. Pat. No. 3,641,349, a characteristic of a web or sheet material being manufactured by a paper making machine can be measured by mounting sensors and detectors on a carriage. The carriage moves in a cross direction while the sheet material is moving in a machine direction which is perpendicular to the cross direction. FIG. 1 illustrates a scanner 10 which includes a framework 11 which has a pair of spaced upper and lower parallel beams 12 and 13 which extend laterally of the sheet material or paper indicated at 14 which is being produced by the paper making machine (not shown). The sheet 14 travels through the scanner in the direction as shown by the arrow 16. Upper and lower gauging heads 17 and 18 are provided in the framework 11 and are adapted to travel longitudinally of the framework 11 and transversely of the sheet 14. Specifically, the sheet 14 travels through the gap 19 provided between the gauging heads 17 and 18. The drive for the gauging heads is such that they can be moved off sheet or in other words, off to the side of the sheet during each direction of travel.

The apparatus 20 of the present invention is as illustrated in FIG. 2, in which a housing 22 in the upper gauging head 17 is located to one side of the sheet 14. The housing 22 is comprises of a first dome 24 and a second dome 26, both substantially hemispherical in shape, and an annular member 28, which is substantially flat. The inside of the first dome 24 can be a reflective, or diffusive or specular surface. The second dome 26 is a window. The first dome 24 and the second dome 26 are concentric with the annular member 28 connecting therebetween. The housing 22 is positioned such that the annular member 28 is nearly parallel to the sheet 14 and is in closer proximity to said sheet 14 than the first dome 24 or the second dome 26. A source 30 in the housing 22 is capable of emitting a beam of electromagnetic radiation 32. For measurment of color or brightness, a ring-shaped xenon pulsed tube manufactured and sold by ILC Technology is preferred. The beam 32 from the source 30 is directed to pass through the second dome 26 to impinge the sheet 14 (shown as a dotted line). The light from the source 30, not in direct alignment with the sheet 14, will be reflected from the first dome 24 onto the sheet 14. The radiation from the source 30 is capable of being absorbed and being reflected by the sheet 14. A portion of the radiation reflected from the sheet 14 (the reflected beam 34) is collected by a collector, comprising a lens 36 and a fiber optic 38. The reflected beam 34 follows a path generally shown as a dash-dot-dash line. The lens 36 focuses the reflected beam 34 onto one end of the fiber optic 38 in the housing 22. The lens 36 is located in or near the second dome 26. The fiber optic 38 is passed from the housing 22. At the other end of said fiber optic 38 the reflected beam 34 is aligned to impinge a grating 40 and reflected therefrom onto a detector 42. The grating 40 is used in the measurement of color of the sheet 14 whereby the color spectrum of the reflected beam 34 is spread out and is incident onto the detector 42. The detector 42 may be a diode array. An air inlet 44 is in the first dome 24. The inlet 44 permits air to enter the housing 22. A plurality of air outlets 46 are located in the annular member 28. The outlets 46 permit air to leave the housing 22 at a constant pressure and to impinge the sheet 14 at a direction substantially perpendicular to the sheet 14.

A standardization member 50 is located on the other side of said sheet 14. The standardization member 50 is substantially flat and is parallel to the sheet 14. The standardization member 50 has a surface 52 facing the sheet 14 which has a known reflective response to the incident beam 32. During standardization, i.e., when the sheet 14 is not between the upper and lower gauging heads 17 and 18, and the gauging heads 17 and 18 are to one side of the framework 11, the beam 32 is aligned to impinge the surface 52 of the standardization member 50. The reflected beam 34, reflected from the surface 52, is used to compare it to the known standard. This comparison serves to correct problems such as electronics drift, lamp aging and dirt on the lens 36. Air outlets 54 in the member 50 permit air to impinge the sheet 14 at a direction substantially perpendicular to the sheet 14. The outlets 50 are in substantial linear alignment with the outlets 46 of the housing 22.

In operation of the apparatus 20 of the present invention, air, under pressure, is introduced into the housing 22 through the inlet 44. The air, under constant pressure, exits from the housing 22 through the outlets 46. The air is directed to impinge the sheet 14 at a direction substantially perpendicular to the sheet 14. Under constant pressure, the air will keep the housing 22 at a constant distance from the sheet 14. Similarly, air under constant pressure is directed from the standardization member 50 to impinge the sheet 14 at a direction substantially perpendicular to the sheet 14 and in linear alignment with the outlets 46 of the first housing 22. The impingement of air on the sheet 14 will maintain the standardization member 50 at a constant distance from the sheet 14. During the operation of the apparatus 20, the source 30 emits a beam of radiation 32 directed to impinge the sheet 14. The reflected beam 34 is collected by lens 36 which is focused onto one end of the fiber optic 38. The other end of the fiber optic 38 is aligned to direct the reflected beam 34 to impinge the detector 42. Various properties of the sheet, such as color or brightness, can be analyzed through the proper selection of the spectral frequency of the beam of radiation of the source 30 and the spectral response of the detector 42.

During standardization the apparatus 20 is moved off sheet, i.e., the sheet 14 is removed. Since the air from the housing 22 will no longer impinge the sheet 14 to "lift" the housing 22 from the sheet, and since the air from the standardization member 50 will also no longer impinge the sheet 14, the housing 22 and the standardization member 50 will move closer to one another until the distance therebetween is substantially the same as the distance between the housing 22 and the sheet 14. In short, the standardization member 50, relative to the housing 22, will move to the position previously located by the sheet 14.

In general, the housing 22 can be of any geometric shape. Since the air must impinge the sheet 14 and "lift" the housing 22, the lighter the housing 22 is the less the amount of air must be expended. The use of the collector, comprising the lens 36 and the fiber optic 38 to gather the reflected beam 34 and to align it to impinge the detector 42, which is not in the housing 22 is to lighten the weight of the housing 22. The housing 22 is only a convenience to hold the source 30 and the collector. The source 30 and the lens 36 and fiber optic 38 may be in any geometic configuration. It should be noted that to further lighten the weight of the housing 22, the source 30 may be located outside the housing 22 with fiber optics connecting the source 30 to the housing 22 to direct the light to impinge the sheet 14. The source 30 can produce any type of electromagnetic radiation, including infrared and ultraviolet. For measurement of color, a D65 source (North Sky Daylight) is preferred. (D65 is a standard set by CIE-Commission Internationale de l'Eclairage.)

It is thus seen that the advantages of the apparatus 20 of the present invention are: First, the apparatus may be used to scan across the width of the sheet, i.e., the apparatus 20 may be mounted on a carriage as shown in FIG. 1 and moved across the width of the sheet. Secondly, it is seen that the apparatus 20 (both the housing 22 as well as the standardization member 50) is each kept at a constant distance from the sheet 14 and thus the apparatus is insensitive to flutter of the sheet, i.e., the unpredictable movement of the sheet 14 along a direction having a component which is perpendicular to the sheet. Lastly, the apparatus finds many more possible uses than the apparatus of the prior art.

What is claimed is:

1. An apparatus to measure select properties of a moving sheet, said apparatus, insensitive to the flutter of said sheet, comprising:
    a source to one side of said sheet capable of emitting a beam of electromagnetic radiation;
    said beam aligned to impinge said sheet;
    said radiation selected such that said beam is capable of being absorbed and being reflected by said sheet;
    a collector to one side of said sheet capable of receiving a portion of said beam reflected from said sheet;
    a detector capable of measuring said select properties of said sheet based upon said radiation received by said collector;
    first means for spacing said source and said collector a constant distance from said sheet;
    a standardization member to the side of said sheet opposite said collector; and
    second means for spacing said standardization member a constant distance from said sheet, said second means including a source of fluid to direct a stream of fluid from said standardization member to impinge the moving sheet.

2. The apparatus of claim 1 wherein said source and said collector are in a housing.

3. The apparatus of claim 1 wherein said first means includes a source of fluid to direct a stream of fluid to impinge said sheet along a direction substantially perpendicular to said sheet.

4. The apparatus of claim 3 wherein second means is constructed and arranged so that the stream of fluid from said standardization member is directed to impinge said sheet along a direction substantially perpendicular to said sheet and in linear alignment with, the stream of fluid from said first means.

5. The apparatus of claim 4 wherein said collector is a lens and a fiber optic, wherein said lens is positioned to focus a portion of said beam reflected from said sheet onto one end of said fiber optic, and said other end of said fiber optic aligned to impinge said detector.

6. The apparatus of claim 5 wherein said radiation is in the visible portion of the electromagnetic spectrum.

* * * * *